United States Patent [19]

Szelenyi et al.

[11] Patent Number: 4,596,811
[45] Date of Patent: Jun. 24, 1986

[54] HETEROCYCLIC COMPOUNDS, A PROCESS FOR THEIR PRODUCTION AND MEDICAMENTS CONTAINING THESE COMPOUNDS

[75] Inventors: Istvan Szelenyi, Schwaig; Stefan Postius, Nuremberg; Helmut Schickaneder, Eckental; Herbert Hansen, Schwabach, all of Fed. Rep. of Germany

[73] Assignee: Ludwig Heumann & Co., GmbH, Nuremberg, Fed. Rep. of Germany

[21] Appl. No.: 543,132

[22] Filed: Oct. 18, 1983

[30] Foreign Application Priority Data

Oct. 20, 1982 [DE] Fed. Rep. of Germany ....... 3238867

[51] Int. Cl.⁴ .................... A61K 31/44; A61K 31/38; C07D 417/12; C07D 333/20
[52] U.S. Cl. .................................. 514/326; 514/422; 514/438; 514/342; 514/365; 514/637; 564/86; 564/102; 546/212; 546/209; 548/197; 548/527; 549/75
[58] Field of Search ................. 564/86, 102; 546/212; 548/527; 549/75; 514/326, 422, 438

[56] References Cited

U.S. PATENT DOCUMENTS 3,853,913 12/1974 Brack et al. ........................... 564/86
3,953,492 4/1976 Mrozik ................................... 564/86
4,083,866 4/1978 Petitpierre ............................ 564/86
4,239,769 12/1980 Price et al. ............................ 549/65
4,283,408 8/1981 Hirata et al. ........................ 548/197
4,362,736 12/1982 Hirata et al. ........................ 548/193

FOREIGN PATENT DOCUMENTS 741364 8/1966 Canada .................................. 564/86
0002930 7/1979 European Pat. Off. ............. 549/65
2821409 11/1978 Fed. Rep. of Germany ........ 549/65
3008056 9/1980 Fed. Rep. of Germany ...... 548/197
538822 8/1941 United Kingdom .................. 564/86

OTHER PUBLICATIONS

Chemical Abstracts, vol. 96, p. 746, (1982), No. 217,853x.
Chemical Abstracts, vol. 97, p. 108, (1982), No. 33922h.

*Primary Examiner*—Robert T. Bond
*Attorney, Agent, or Firm*—Burns, Doane, Swecker & Mathis

[57] ABSTRACT

The invention relates to special heterocyclic compounds corresponding to general tautomeric formula I which are distinguished by improved antagonistic activity on histamine-$H_2$-receptors. The invention also relates to a process for producing these compounds and to medicaments containing them.

19 Claims, No Drawings

HETEROCYCLIC COMPOUNDS, A PROCESS FOR THEIR PRODUCTION AND MEDICAMENTS CONTAINING THESE COMPOUNDS

This invention relates to new amidine derivatives with an effect on histamine-$H_2$-receptors, to a process for their production and medicaments containing these compounds and, finally, to the use of these compounds for therapeutic purposes.

By virtue of their $H_2$-antagonistic activity, the compounds obtainable in accordance with the invention inhibit the secretion of stomach acid where it is stimulated by histamine agonists (Ash and Schild "Brit. J. Pharmacol. Chemother." 27, 427 (1966) and Black et al "Nature" 236, 385 (1972). The pharmacological activity of these compounds, which is described in more detail hereinafter, can be demonstrated in perfused rats' stomachs by a modified method according to DE-OS No. 27 34 070. In addition, the $H_2$-antagonistic effect can be demonstrated in conscious Heidenhain pouch dogs by the method of Black et al "Nature" 236, 385 (1971). The new compounds also antagonize the effect of histamine on the frequency of contraction of the isolated left atrium of guinea pigs, but do not affect histamine-induced contractions of the isolated, smooth, gastrointestinal muscle where they are produced by $H_1$-agonists.

Since inhibitors for histamine-$H_2$-receptors have an inhibiting effect both on the basal secretion of stomach acid and also on gastrin-, histamine-, methacholine- or food-induced secretion of stomach acid, they may be used in the treatment of peptic ulcers caused by excessive secretion of stomach acid and also in the treatment of hyperacidic gastritis.

The object of the present invention is to provide new inhibitors for histamine-$H_2$-receptors showing improved activity.

This object is achieved by the present invention. The present invention relates to heterocyclic compounds corresponding to the following general tautomeric formulae $$R^1R^2NAlk-Q-XY(CH_2)_m-\overset{NH}{\overset{\|}{C}}-NH-\overset{O}{\underset{\underset{O}{\|}}{\overset{\|}{S}}}-R^3 \rightleftharpoons \quad (I)$$

$$R^1R^2NAlk-Q-XY(CH_2)_m-\overset{NH_2}{\overset{|}{C}}=N-\overset{O}{\underset{\underset{O}{\|}}{\overset{\|}{S}}}-R^3$$

in which $R^1$ represents linear $C_{1-6}$alkyl or cycloalkyl and
$R^2$ represents linear $C_{1-6}$alkyl;
$R^1$ or and $R^2$ together with the nitrogen atom to which they are attached form a 5- or 6-membered ring;
Alk represents a straight-chain alkylene chain containing from 1 to 6 carbon atoms;
Q represents a thiophene ring incorporated in the rest of the molecule by bonds in the 2- and 5-position or in the 2- and 4-position, or
Q represents a thiazole ring incorporated in the rest of the molecule by bonds in the 2- and 4-position or
Q represents a benzene ring incorporated in the rest of the molecule by bonds in the 1- and 3-position;
X, where Q is thiophene or thiazole, represents methylene;
Y represents sulfur and m=2 or 3;
X, where Q is benzene, represents oxygen, Y is a single bond and m=3 or 4;
$R^3$ is an amino group or an arylamino group;
and to physiologically acceptable salts thereof.

One preferred group of compounds according to the invention is characterized in that $R^1$ represents $C_{1-3}$alkyl or $C_{5-6}$cycloalkyl and $R^2$ represents hydrogen, methyl or ethyl or $R^1R^2N$ represents a 5- to 6-membered ring.

Other preferred groups of compounds according to the invention are characterized in that Q is a thiophene ring incorporated in the rest of the molecule by bonds in the 2- and 5-position, and in that the group $XY(CH_2)_m$ represents $CH_2$-S-$(CH_2)_{2-3}$ or in that Q represents a thiophene or thiazole ring incorporated in the rest of the molecule by bonds in the 2- and 4-position and in that the group $XY(GH2)_m$ represents $CH_2$-S-$(CH_2)_{2-3}$ or in that Q represents a benzene ring incorporated by bonds in the 1- and 3-position and in that the group $XY(CH_2)_m$ represents $O(CH_2)_{3-4}$.

In general formula I, $R^1$ represents a linear $C_{1-6}$-alkyl group, preferably a linear $C_{1-3}$alkyl a group and more preferably a methyl or ethyl group. $R_2$ represents a linear $C_{1-6}$alkyl group, preferably a linear $C_{1-3}$alkyl group and more preferably a methyl or ethyl group. The substituents $R_1$ and $R_2$ independently of one another may be selected from the groups mentioned above. $R_1$ and $R^2$ may also form, together with the nitrogen atom to which they are attached, a 5-membered or 6-membered ring, for example a pyrrolidino or piperidino ring, preferably a piperidino ring.

Alk is a linear alkyl chain containing from 1 to 6 carbon atoms, preferably from 1 to 3 carbon atoms, and more particularly a methylene group.

Q is a thiophene, thiazole or benzene ring. The thiophene ring may be incorporated in the rest of the molecule by bonds in the 2- and 5-position or in the 2- and 4-position. Compounds in which the thiophene ring is incorporated in the 2- and 4-position are preferred. The thiazole ring is incorporated in the rest of the molecule by bonds in the 2- and 4-position whereas the benzene ring is incorporated in the rest of the molecule by bonds in the 1- and 3-position.

Where Q is a thiophene or thiazole ring, X is the methylene group and Y is a sulfur atom. In that case, m has the value 2 or 3.

Where Q is a benzene ring, X is an oxygen atom and Y is a single bond. In that case, m has the value 3 or 4.

$R^3$ represents an amino group or an arylamino group, more particularly the p-aminophenyl group.

The compounds according to the invention are produced by a process which is characterized in that a compound corresponding to the following general formula $$R^1R^2NAlk-Q-XY(CH_2)_m-\overset{NH}{\overset{\|}{C}}-OCH_3 \quad (II)$$

in which $R^1$, $R^2$, Alk, Q, X, Y and m are as defined above, is reacted in known manner with a sulfonamide corresponding to the following formula

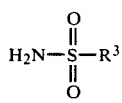

in which $R^3$ as defined above, and the compound obtained is optionally converted into a physiologically acceptable salt.

In this process, a compound corresponding to general formula II is reacted with a sulfonamide of general formula III to the form the desired compounds. The reaction is carried out in a solvent and at a temperature from room temperature to the boiling temperature of the solvent used. Suitable solvents are, for example, alcohols, such as methanol or ethanol, ethers, such as dioxane or tetrahydrofuran, and halogenated hydrocarbons, such as carbon tetrachloride or chloroform. The reaction product is worked up in known manner, for example by concentrating the reaction mixture and separating off the compound obtained by chromatography. The support used for chromatographic separation may be, for example, a non-ionic adsorbent, such as silica gel, etc. The eluent used may be, for example, a mixture of alcohol and halogenated hydrocarbon, such as for example methylene chloride-methanol, in a ratio by volume of 8:2.

The compounds according to the invention may be converted into physiologically acceptable salts with suitable acids. This reaction is carried out in known manner.

Suitable acids are inorganic and organic acids. Examples of inorganic acids are hydrochloric acid and hydrobromic acid. Examples of suitable organic acids are oxalic acid, malic acid and succinic acid. In principle, any pharmaceutically suitable inorganic and organic acids may be used for conversion into the phsyiologically acceptable salt.

The compounds according to the invention corresponding to general formula I readily form acid addition salts and there are tautomeric forms of these compounds in the

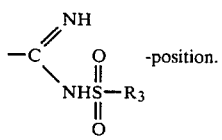 -position.

Accordingly, the present invention also relates to the production of the acid addition salts and tautomeric forms of the compounds of general formulae I.

The compounds N-(p-aminobenzene-sulfonyl)-[(2-N,N-dimethylaminomethylthienyl-4)-methylthio]-propionamidine, N-(p-aminobenzene-sulfonyl)-3-[(2-piperidinylmethylthienyl-4)-methylthio]-propionamidine, N-(p-aminobenzene-sulfonyl)-3-[(2-N,N-dimethylaminomethylthiazol-4-yl)-methylthio]-propionamidine and N-(p-aminobenzene-sulfonyl)-4-[(3-piperidinylmethyl)-phenoxy]-butyroamidine and their physiologically acceptable acid addition salts are preferred. N-(p-aminobenzene-sulfonyl)-3-[(2-N,N-dimethylaminomethylthienyl-4)-methylthio]-propionamidine, N-(p-aminobenzenesulfonyl)-3-[(2-piperidinylmethylthienyl-4)-methylthio]propionamidine and their physiologically acceptable salts are particularly preferred.

The compounds according to the invention, preferably in the form of a salt, may be formulated in any way for administration. Accordingly, the present invention also relates to medicaments containing at least one compound according to the invention for use in human or veterinary medicine. Medicaments of the type in question may be conventionally produced using one or more pharmaceutically acceptable supports or diluents.

Accordingly, the compounds according to the invention may be formulated for oral, buccal, topical, parenteral or rectal administration, oral administration being preferred. For oral administration, the medicament may assume the form of, for example, tablets, capsules, powders, solutions, syrups or suspensions prepared conventionally using acceptable diluents. For buccal administration, the medicament may assume the form of tablets or packets produced in the usual way.

The compounds according to the invention may be formulated for parenteral administration by bolus injection or continuous infusion. Formulations for injection may be made up in dose unit form as ampoules or in the form of multiple-dose containers with added preservative. The medicaments may assume such forms as suspensions, solutions or emulsions in oily or aqueous vehicles and may contain formulation aids, such as suspension agents, stabilizers and/cr dispersants. Alternatively, the active principle may even be in powder form for reconstitution with a suitable vehicle, for example sterile pyrogen-free water, before use.

The compounds according to the invention may also be formulated for rectal preparations, for example suppositories or enemas, containing for example conventional suppository bases, such as cocoa butter or other glycerides.

For topical application, the compounds according to the invention may be formulated in the usual way as ointments, creams, gels, lotions, powders or sprays.

For oral administration, a suitable daily dose of compounds according to the invention is 1–4 doses containing a total of 5 mg to 1 g/day and preferably 5 to 250 mg/day, depending on the condition of the patient. In individual cases, it may be necessary to deviate from these doses depending on the behavior of the individual with respect to the active principle or its formulation and on the time at which or period for which the active principle is administered. For example, there are cases where less than the minimum dose mentioned above is sufficient, whereas in other cases it will be necessary to exceed the upper limit indicated.

The compounds according to the invention are distinguished from reputedly good medicaments acting in the same direction by an improvement in the pharmacological activities. This is apparent from the results of the comparative pharmacological tests described in the following.

An accepted method for determining H2-antagonistic activity is to determine the pA2-values in vitro on the isolated atrium of guinea pigs (cf. Ariens, Molecular Pharmacology, Vol. 1, Academic Press, New York, 1964).

|  | pA$_2$-values |
| --- | --- |
| Cimetidine: | 6.3 (comparison) |
| Example 2: | 7.10 |
| Example 10: | 6.95 |
| Example 12: | 7.20 |

Other compounds corresponding to general formula I show similar pharmocological effects.

EXAMPLE 1

N-sulfamoyl-3-[(2-N,N-dimethylaminoethylthienyl-4)-methylthiop]-propionamidine

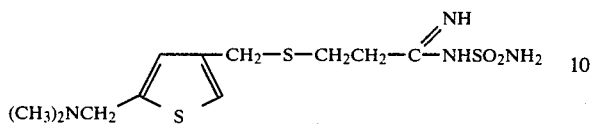

2.40 g (25 mMoles) of sulfamide are added to a solution of 2.56 g (10 mMoles) of methyl-3-[(2-N,N-dimethylaminomethyl-thienyl-4)-methylthio]-propionimidate and 30 ml of methanol, followed by reaction under reflux for 8 hours. The solvent is then distilled off in vacuo and the residue purified by column chromatography (silica gel; eluent: methylene chloride/methanol 80:20).

Colorless oil. $R_f = 0.2 (CH_2Cl_2/MeOH\ 90:10)$.

EXAMPLE 1a

Production of methyl-3-[(2-N,N-dimethylaminomethylthienyl-4)-methylthio]-propionimidate Methyl-3-(2-N,N-dimethylaminomethylthienyl-4-methylthio]-propionimidate is produced by reacting 2-(N,N-dimethylaminomethyl)-4-S-isothiourea methylthiophene dihydrochloride with equimolar quantities of chloropropionitrile in aqueous alkaline solution at 0°–10° C. The [(2-(N,N-dimethylaminomethylthio)-4-thienylemthylthio]-propionitrile -propiontrile obtained is reacted with dry hydrogen chloride at 0° C. in anhydrous methanol to form methyl-3-[(2-N,N-dimethylaminomethylthienyl-4)-methylthio]-propionimidate.

EXAMPLE 2

N-(p-aminobenzene-sulfonyl)-3-[(2-N,N-dimethylaminomethylthienyl-4)-methylthio]-propionamidine

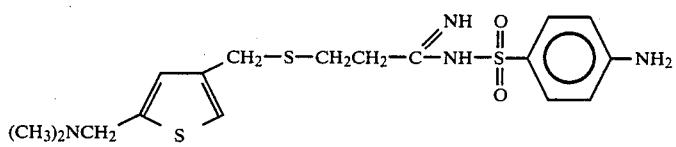

The reaction is carried out as in Example 1 with 2.72 g (19 mMoles) of methyl-3-[(2-N,N-dimethylaminomethylthienyl-4)-methylthio]-propionimidate and 4.3 g (25 mMoles) of p-aminobenzene sulfonamide. Colorless oil. $R_f = 0.4\ (CH_2Cl_2/MeOH\ 80:20)$.
Yield: 2.3 g (56%).
$C_{17}H_{24}N_4O_2S_3$ (412) Calculated: C: 49.51, H: 5.83, N: 13.59; Observed; C:49.35, H:5.78, N:13.31.

Yield: 1.51 g (45%).
$C_{11}H_{20}N_4S_3O_2$ (336) Calculated: C: 39.28, H: 5.95, N: 16.67, Observed: C: 38.94, H: 6.12, N: 16.71.

| $^1$H—NMR-spectrum: ($d_6$-DMSO, TMS as internal standard) | δ = | |
|---|---|---|
| | 2.13 | (s) ((CH$_3$)$_2$—N) 6H, |
| | 2.27–2.77 | (m) (—(CH$_2$)$_2$—) 4H, |
| | 3.53 | (s) (S—CH$_2$) 2H, |
| | 3.67 | (s) (N—CH$_2$) 2H, |
| | 6.43 | (s) (—SO$_2$NH$_2$) 2H (exchangeable with D$_2$O) |
| | 6.87 | (s) (aromatic-H) 1H, |
| | 7.20 | (s) (aromatic-H) 1H, |
| | 7.30 | (s) (NH—SO$_2$) 1H (exchangeable with D$_2$O) |
| | 8.20 | (s) (=N—H) 1H (exchangeable with D$_2$O) ppm |

| $^1$H—NMR-spectrum: ($d_6$-DMSO, TMS as internal standard) | δ = | |
|---|---|---|
| | 2.17 | (s) ((N—CH$_3$)$_2$) 6H, |
| | 2.40–2.67 | (m) (—(CH$_2$)$_2$—) 4H, |
| | 3.53 | (s) (S—CH$_2$) 2H, |
| | 3.63 | (s) (N—CH$_2$) 2H, |
| | 5.77 | (s) (—NH$_2$) 2H (exchangeable with D$_2$O), |
| | 6.53 | (d) (aromatic-H) 2H, |
| | 6.83 | (s) (aromatic-H) 1H, |
| | 7.13 | (s) (aromatic-H) 1H, |
| | 7.43 | (d) (aromatic-H) 2H, |
| | 7.73 | (s) (=NH—SO$_2$) 1H exchangeable with D$_2$O |
| | 8.40 | (s) (=NH) 1H (exchangeable with D$_2$O) ppm |

EXAMPLE 3

N-sulfamoyl-3-[(2-N,N-dimethylaminomethylthiazol-4-yl)-methylthio]-propionamidine

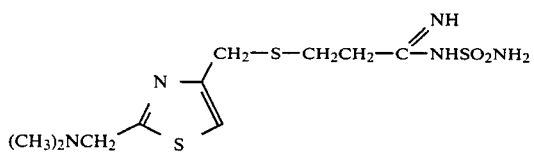

The reaction is carried out as in Example 1 with 2.73 g (10 mMoles) of methyl-3-[(2-N,N-dimethylaminomethylthiazol-4-yl)-methylthio]-propionimidate and 2.40 g (25 mMoles) of sulfamide.

Colorless oil. $R_f=0.2$ ($CH_2Cl_2$/MeOH 90:10).
Yield 1.28 g (38%).
$C_{10}H_{19}N_5S_3O_2$ (337) Calculated: C: 35.61, H: 5.64, Observed: C: 35.28, H: 5.79.

| $^1$H—NMR-spectrum: (d$_6$-DMSO, TMS as internal standard) | $\delta =$ | 2.27 | (s) ((C$\underline{H_3}$)$_2$N—) 6H, |
|---|---|---|---|
| | | 2.33–2.83 | (m) (—(C$\underline{H_2}$)$_2$—) 4H, |
| | | 3.73 | (s) (N—C$\underline{H_2}$—) 2H, |
| | | 3.83 | (s) (—S—C$\underline{H_2}$—) 2H, |
| | | 6.50 | (s) (—SO$_2$—N$\underline{H_2}$) 2H (exchangeable with D$_2$O) |
| | | 7.40 | (s) (—N$\underline{H}$SO$_2$—) 1H (exchangeable with D$_2$O) |
| | | 7.47 | (s) (aromatic-$\underline{H}$), |
| | | 8.27 | (s) (=N—$\underline{H}$) 1H (exchangeable with D$_2$O) ppm |

Methyl-3-[(2-N,N-dimethylaminomethylthiazol-4-yl)-methylthio]-propionimidate is produced with the corresponding starting compounds as in Example 1a.

EXAMPLE 4

N-(p-aminobenzene-sulfonyl)-3-[(2-N,N-dimethylaminomethylthiazol-4-yl)-methylthio]-propionamidine

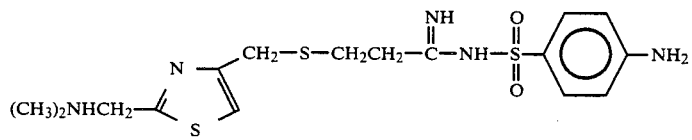

The reaction is carried out as in Example 1 with 2.73 g (10 moles) of methyl-3-[(2-N,N-dimethylaminomethyl-thiazol-4-yl) -methylthio]-propionimidate and 4.3 g (25 mMoles) of p-amionbenzene sulfonamide.

Colorless oil. $R_f=0.3$ ($CH_2Cl_2$/MeOH 90:19).
Yield: 2.40 g (58%).
$C_{16}H_{23}N_5S_3O_2$ (412) Calculated: C: 46.49, H: 5.57, N: 16.95, Observed: C: 46.78, H: 5.51, N: 16.72.

| $^1$H—NMR-spectrum: (d$_6$-DMSO, TMS as internal standard) | $\delta =$ | 2.23 | (s) ((C$\underline{H_3}$)$_2$N—) 6H, |
|---|---|---|---|
| | | 2.33–2.80 | (m) (—(C$\underline{H_2}$)$_2$—) 4H |
| | | 3.73 | (s) (N—C$\underline{H_2}$) 2H, |
| | | 3.80 | (s) (—SC$\underline{H_2}$—) 2H, |
| | | 5.77 | (s) (—N$\underline{H_2}$) 2H (exchangeable with D$_2$O) |
| | | 6.57 | (d) (aromatic-$\underline{H}$) 2H, |
| | | 7.33 | (s) (aromatic-$\underline{H}$) 1H, |
| | | 7.47 | (d) (aromatic-$\underline{H}$) 2H, |
| | | 7.80 | (s) (—N$\underline{H}$SO$_2$—) 1H exchangeable with D$_2$O) |
| | | 8.40 | (s) (=N—$\underline{H}$) 1H (exchangeable with D$_2$O) ppm |

EXAMPLE 5

N-sulfamoyl-4-[(3-N,N-dimethylaminomethyl)-phenoxy]- butyroamidine

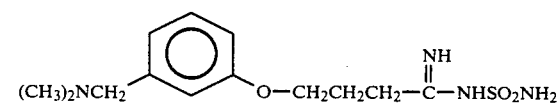

The reaction is carried out as in Example 1 with 2.50 g (10 mMoles) of methyl-4-[(3-N,N-dimethylaminomethyl)-phenoxy]-butyroamidate and 2.40 g (25 mMoles) of sulfamide.

Light yellow oil. $R_f=0.2$ ($CH_2Cl_2$/ MeOH 50:50).
Yield: 0.88 g (28%).
$C_{13}H_{22}N_4O_3S$ Calculated: C: 49.68, H: 7.01, N: 17.83, Observed: C: 49.37, H: 6.82, N: 17.20.

| $^1$H—NMR-spectrum: (d$_6$-DMSO, TMS as internal standard) | $\delta =$ | 1.80–2.53 | (m) (—C$\underline{H_2}$—C$\underline{H_2}$—) 4H |
|---|---|---|---|
| | | 2.17 | (s) ((C$\underline{H_3}$)$_2$N—) 6H, |
| | | 3.40 | (s) (N—C$\underline{H_2}$) 2H, |
| | | 4.00 | (t) (—OC$\underline{H_2}$) 2H, |
| | | 6.50 | (s) (—N$\underline{H_2}$) 2H (exchangeable with D$_2$O) |
| | | 6.67–7.40 | (m) (aromatic-$\underline{H}$) 4H, |
| | | 7.40 | (s) (N$\underline{H}$SO$_2$—) 1H (exchangeable with D$_2$O) |
| | | 8.30 | (s) (=N—$\underline{H}$) 1H (exchangeable with D$_2$O) ppm |

EXAMPLE 5a

Production of methyl-4-[(3-N,N-dimethylaminomethyl)phenoxy]-butyroimidate

Methyl-4-[(3-N,N-dimethylaminomethyl)-phenoxy]-butyroimidate is produced by reacting 3-(dimethylaminomethyl,-phenol in anhydrous dimethylformamide with NaH and 4-chlorobutyronitrile to form 3-N,N-dimethylaminomethyl phenoxybutyronitrile which is subsequently reacted with dry hydrogen chloride at 0°–10° C. in a mixture of methanol and chloroform to form methyl-4-[(3-N,N-dimethylaminomethyl)-phenoxy]-butyroimidate.

EXAMPLE 6

N-(p-aminobenzene-sulfonyl)-4-[(3-N,N-dimethylaminomethyl)-phenoxy]-butyroamidine

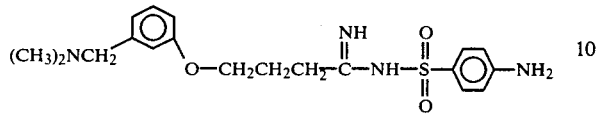

The reaction is carried out as in Example 1 with 2.50 g (10 mMoles) of methyl-4-[(3-N,N-dimethylaminomethyl)-phenoxy]-butyroimidate and 4.3 g (25 mMoles) of p-aminobenzene sulfonamide.

Colorless oil. $R_f=0.4$ ($CH_2Cl_2$/ MeOH 50:50).
Yield: 1.48 g (38%).
$C_{19}H_{26}N_4O_3S$ Calculated: C: 58.44, H: 6.71, N: 14.34, Observed: C: 58.14, H: 6.74, N: 14.06.

| $^1$H—NMR-spectrum: | $\delta =$ | 1.87 | (m) (—$CH_2$—) 2H, |
|---|---|---|---|
| (d$_6$-DMSO, TMS as | | 2.13 | (s) (N—(CH$_3$)$_2$) 6H, |
| internal standard | | 2.37 | (t) (C—$CH_2$) 2H, |
| | | 3.37 | (s) (N—$CH_2$) 2H, |
| | | 3.87 | (t) (—O—$CH_2$) 2H, |
| | | 5.80 | (s) (—$NH_2$) 2H (exchangeable with D$_2$O) |
| | | 6.60 | (d) (aromatic-$H$) 2H, |
| | | 6.73–7.33 | (m) (aromatic-$H$) 4H. |
| | | 7.50 | (d) (aromatic-$H$) 2H, |
| | | 7.77 | (s) (—N$H$—SO$_2$) 1H (exchangeable with D$_2$O) |
| | | 8.47 | (s) (—N$H$) 1H (exchangeable with D$_2$O) ppm |

EXAMPLE 7

N-sulfamoyl-4-[(3-piperidinylmethyl)-phenoxy]-butyroamidine

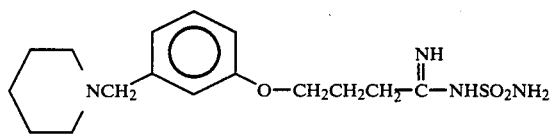

The reaction is carried out as in Example 1 with 2.90 g (10 mMoles) of methyl-4-[(3-piperidinylmethyl)-phenoxy]-butyroimidate and 2.40 g (25 mMoles) of sulfamide.

Colorless oil. $R_f=0.3$ ($CH_2Cl_2$/ MeOH 80:20).
Yield: 1.06 g (30%).
$C_{16}H_{26}N_4O_3S$ (354).

| $^1$H—NMR-spectrum: | $\delta =$ | 1.43 | (s, broad) (—(CH$_2$)$_3$—) 6H, |
|---|---|---|---|
| (d$_6$-DMSO, TMS as | | 2.0 | (m) (—CH$_2$—$CH_2$—CH$_2$) 2H, |
| internal standard) | | 2.33 | (s, broad) (N(CH$_2$)$_2$—; —$CH_2$) 6H |
| | | 3.43 | (s) (N—$CH_2$) 2H, |
| | | 4.00 | (t) (—O—$CH_2$) 2H, |
| | | 6.47 | (s) (—SO$_2$$NH_2$) 2H (exchangeable with D$_2$O) |
| | | 6.67–7.30 | (m) (aromatic-$H$) 4H |
| | | 7.33 | (s) (N$H$—SO$_2$) 1H (exchangeable with D$_2$O) |
| | | 8.23 | (s) (=N—$H$) 1H (exchangeable with D$_2$O) ppm |

Methyl-4-[(3-piperidinylmethy)-phenoxy]-butyroamidate is produced as in Example 5a from 3-(piperidinylmethyl)-phenol and 4-chlorobutyronitrile, followed by reaction with hydrogen chloride.

EXAMPLE 8

N-(p-aminobenzene-sulfonyl)-4-[(3-piperidinylmethyl)-phenoxy]-butyroamidine

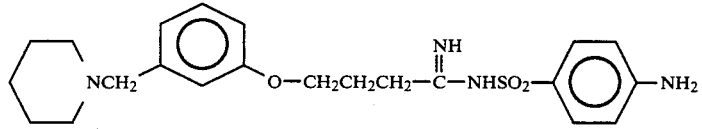

The reaction is carried out as in Example 1 with 2.90 g (10 mMoles) of methyl-4-[(3-piperidinylmethyl)-phenoxy]-butyroimidate and 4.30 g (25 mMoles) of p-aminobenzene sulfonamide.

Light yellow oil. $R_f=0.3$ ($CH_2Cl_2$/MeOH 80:20).
Yield: 1.5 g (35%).
$C_{22}H_{30}N_4O_3S$ Calculated: C: 61.39, H: 6.98, N: 13.02, Observed: C: 61.44, H: 6.96, N: 12.84.

| $^1$H—NMR-spectrum: | $\delta =$ | 1.43 | (s, broad) (—(CH$_2$)$_3$—) 6H |
|---|---|---|---|
| (d$_6$-DMSO, TMS as | | 1.90 | (m) (—CH$_2$—$CH_2$—CH$_2$—) 2H |
| internal standard) | | 2.33 | (s, broad) (N(CH$_2$)$_2$; —$CH_2$) 6H |
| | | 3.37 | (s) (N—$CH_2$) 2H, |
| | | 3.87 | (t) (—O—$CH_2$) 2H, |
| | | 5.80 | (s) (—$NH_2$) 2H (exchangeable with D$_2$O) |
| | | 6.60 | (d) (aromatic-$H$) 2H, |
| | | 6.73–7.33 | (m) (aromatic-$H$) 4H, |
| | | 7.50 | (d) (aromatic-$H$) 2H, |
| | | 7.77 | (s) (N$H$SO$_2$) 1H (exchangeable with D$_2$O) |
| | | 8.43 | (s) (=N—$H$) 1H (exchangeable with D$_2$O) ppm |

EXAMPLE 9

N-sulfamoyl-5-[(3-piperidinylmethyl)-phenoxy]-valeroamidine

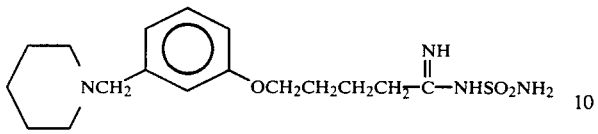

The reaction is carried out as in Example 1 with 3.04 g (10 mMoles) of methyl-5-[(3-piperidinylmethyl)-phenoxy]-valeroimidate and 2.40 g (25 mMoles) of sulfamide.

Yellow oil. $R_f = 0.3$ $CH_2Cl_2/CH_3OH$ 80:20).
Yield: 1.18 g (32%).
$C_{17}H_{28}N_4O_3S$ (369) Calculated: C: 55.41, H: 7.66, N: 15.20, Observed: C: 55.00, H: 7.53, H: 15.60.

| $^1$H—NMR-spectrum: ($d_6$-DMSO, TMS as internal standard) | $\delta =$ 1.43 | (s, broad) (—$(CH_2)_3$—) (—$CH_2$—) 8H, |
|---|---|---|
| | 1.73 | (m) (—$CH_2$—$CH_2$—$CH_2$) 2H, |
| | 2.33 | (s, broad) (N$(CH_2)_2$; $CH_2$—C=NH) 6H |
| | 3.37 | (s) (N—$CH_2$) 2H, |
| | 3.97 | (t) (—O—$CH_2$) 2H, |
| | 6.43 | (s) ($SO_2$—$NH_2$) 2H (exchangeable with $D_2O$ |
| | 6.70–7.33 | (m) (aromatic-$\underline{H}$) 4H, |
| | 7.37 | (s) (N$\underline{H}SO_2$) 1H (exchangeable with $D_2O$) |
| | 8.20 | (s) (=N—$\underline{H}$) 1H (exchangeable with $D_2O$) ppm |

Methyl-5-[(3-piperidinylmethyl)-phenoxy]-valeroimidate produced as in Example 5a from 3-(piperidinylmethyl)-phenol and 5-chlorovalerianic acid nitrile, followed by reaction with hydrogen chloride.

EXAMPLE 10

N-(p-aminobenzene-sulfonyl)-5-[(3-piperidinylmethyl)-phenoxy]-valeroamidine

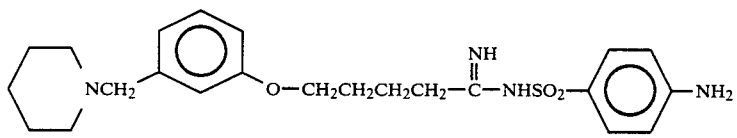

The reaction is carried out as in Example 1 with 3.04 g (10 mMoles) of methyl-5-[83-piperidinylmethyl)-phenoxy]-valeroimidate and 4.30 g (25 mMoles) of p-aminobenzene sulfonamide.

Light yellow oil. $R_f = 0.3$ ($CH_2Cl_2$/MeOH 80:20).
Yield: 1.69 g (38%).
$C_{23}H_{32}N_4O_3S$ (445) Calculated: C: 62 14, H: 7 26, N: 12.60, Observed C: 62.30, H: 7.17, N: 12.65.

| $^1$H—NMR-spectrum: ($d_6$-DMSO, TMS as internal standard) | $\delta =$ 1.43 | (s, broad) (—$(CH_2)_3$—; —$CH_2$) 8H, |
|---|---|---|
| | 1.63 | (m) (—$CH_2$—$CH_2$—$CH_2$) 2H |
| | 2.30 | (s, broad) (N$(CH_2)_2$; $CH_2$—C=NH) 6H, |
| | 3.37 | (s) (N—$CH_2$) 2H, |
| | 3.87 | (t) (O—$CH_2$) 2H, |
| | 5.80 | (s) (—$NH_2$) 2H (exchangeable with $D_2O$) |
| | 6.60 | (d) (aromatic-$\underline{H}$) 2H, |
| | 6.70–7.33 | (m) (aromatic-$\underline{H}$) 4H, |
| | 7.53 | (d) (aromatic-$\underline{H}$) 2H, |
| | 7.73 | (s) (N$\underline{H}$—$SO_2$) 1H (exchangeable with $D_2O$) |
| | 8.37 | (s) (=N—$\underline{H}$) 1H (exchangeable with $D_2O$) ppm |

EXAMPLE 11

N-sulfamoyl-3-[(2-piperidinylmethylthienyl-4)-methylthio]-propionamidine

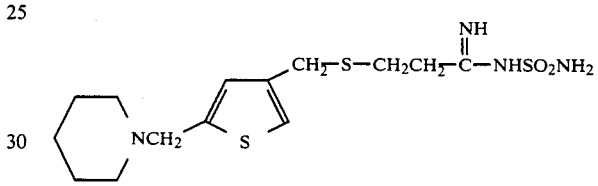

The reaction is carried out as in Example 1 with 3.12 g (10 mMoles) of methyl-3-[(2-piperidinylmethylthienyl-4)-methylthio]-propionimidate and 2.40 g (25 mMoles) of sulfamide.

Colorless oil. $R_f = 0.2$ ($CH_2Cl_2$/MeOH 80:20).
Yield: 0.79 g (21%).

| $^1$H—NMR-spectrum: ($d_6$-DMSO, TMS as internal standard) | $\delta =$ 1.47 | (m, broad) (—$(CH_2)_3$—) 6H |
|---|---|---|
| | 2.13– 2.77 | (m) (—$(CH_2)_2$—, N—$(CH_2)_2$—) 8H, |
| | 3.70 | (s, broad) (—$CH_2$—S, N—$CH_2$) 4H |
| | 6.43 | (s) (—$SO_2NH_2$) 2H (exchangeable with $D_2O$) |
| | 6.80 | (s) (N$\underline{H}$—$SO_2$) 1H (exchangeable with $D_2O$) |
| | 6.93 | (s) (aromatic-$\underline{H}$) 1H, |
| | 7.23 | (s) (aromatic-$\underline{H}$) 1H, |
| | 7.30 | (s) (=N—$\underline{H}$) 1H (exchangeable with $D_2O$) ppm |

Methyl-3-[(2-piperidinylmethylthienyl-4)-methylthio]-propionimidate is produced as in Example 1a from 2-(piperidinylmethyl)-4-S-isothiourea methylthiophene dihydrochloride and equimolar quantities of chloropropionitrile, followed by reaction with methanol-hydrogen chloride.

EXAMPLE 12

N-(p-aminobenzene-sulfonyl)-3-(2-piperidinylmethyl-thienyl-4)-methylthio]-propionamidine

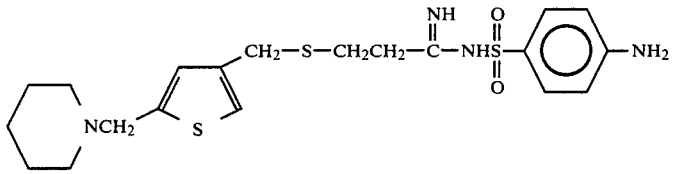

The reaction is carried out as in Example 1 with 3.12 g (19 mMoles) of methyl-3-[(2-piperidinylmethylthienyl-4)-methylthiol]-propionimidate and 4.3 g (25 mMoles) of p-aminobenzene sulfonamide.

Light yellow oil. $R_f=0.2$ ($CH_2Cl_2$/MeOH 90:10). Yield: 1.85 g (41%).

$C_{20}H_{28}N_4O_2S_3$ (452) Calculated: C: 53.10, H: 6.19, Observed: C: 53.42, H: 6.39.

| $^1$H—NMR-spectrum: | δ = 1.47 | (m, broad) (—$(CH_2)_3$—) 6H, |
|---|---|---|
| (d$_6$-DMSO, TMS as | 2.30– | (m) (—$(CH_2)_2$—, |
| internal standard) | 2.73 | N—$(CH_2)_2$ 8H |
| | 3.47 | (s) ($CH_2$—S) 2H |
| | 3.70 | (s) (N—$CH_2$) 2H, |
| | 5.83 | (s) (—$NH_2$) 2H (exchangeable with $D_2O$) |
| | 6.63 | (d) (aromatic-H) 2H, |
| | 6.90 | (s) (aromatic-H) 1H, |
| | 7.20 | (s) (aromatic-H) 1H, |
| | 7.50 | (d) (aromatic-H) 2H, |
| | 7.80 | (s) (N H —$SO_2$) 1H (exchangeable with $D_2O$) |
| | 8.47 | (s) (=N—H) 1H (exchangeable with $D_2O$) ppm |

EXAMPLE 13

N-(p-aminobenzene-sulfonyl)-3-[(2-piperidinylmethyl-thiazol-4-yl)-methylthio]-propionamidine

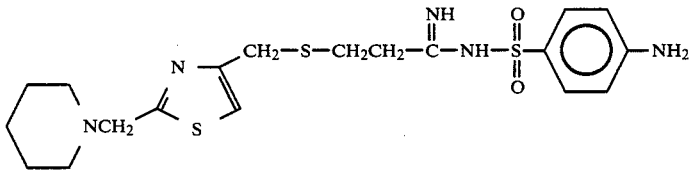

The reaction is carried out as in Example 1 with 3.14 g (10 mMoles) of methyl-3-[2-piperidinylmethylthiazol-4-yl]-propionimidate and 4.3 g (25 mMoles) of p-aminobenzene sulfonamide.

Light yellow oil. $R_f=0.7$ ($CH_2Cl_2$/MeOH 90:10). Yield: 1.45 g (32%).

$C_{20}H_{28}N_4O_2S_3$ (453) Calculated: C: 50.33, H: 5.96, N: 15.45, Observed: C: 50.32, H: 6.24, N: 15.09.

| $^1$H—NMR-spectrum: | = 1.47 | (m, broad) (—$(CH_2)_3$—) 6H, |
|---|---|---|
| (d$_6$-DMSO, TMS as | 2.30– | (m) (—$(CH_2)_2$—, |
| internal standard) | 2.80 | N—$(CH_2)_2$—) 8H, |
| | 3.73 | (s) ($CH_2$—S) 2H, |
| | 3.77 | (s) (N—$CH_2$) 2H, |
| | 5.83 | (s) (—$NH_2$) 2H (exchangeable with $D_2O$) |
| | 6.60 | (d) (aromatic-H) 2H, |
| | 7.33 | (s) (aromatic-H) 1H, |
| | 7.50 | (d) (aromatic-H) 2H, |
| | 7.80 | (s) (N H —$SO_2$) 1H (exchangeable with $D_2O$) |
| | 8.43 | (s) (=N—H) 1H (exchangeable with $D_2O$) ppm |

Methyl-3-[2-piperidinylmethylthiazol-4-yl]-propionimidate is produced as in Example 1a from 2-(piperidinylmethyl)-4-S-isothiourea methylthiazole dihydrochloride and equimolar quantities of chloropropionitrile, followed by reaction with methanol-hydrogen chloride. Examples of medicaments according to the invention are given in the following:

| (a) Tablets | mg/tablet | mg/tablet |
|---|---|---|
| Active principle | 20.0 | 40.0 |
| Microcrystalline cellulose BPC | 99.5 | 199.0 |
| Magnesium stearate | 0.5 | 1.0 |
| Compression weight | 120.0 | 240.0 |

The medicament is sifted through a 250 μm sieve, mixed with the extenders and compressed with 6.5 mm and 8.0 mm diameter stamps for the 20 and 40 mg strengths. The tablets may be film-coated by known methods with suitable film-forming materials, for example methyl cellulose, ethyl cellulose or hydroxypropyl methyl cellulose.

| (b) Capsules | mg/capsule |
|---|---|
| Active principle | 20.0 |
| Sta-R × 1500 starch | 79.5 |
| Magnesium stearate B.P. | 0.5 |
| Filling weight | 100.0 |

The active principle is sifted through a 250μm sieve and mixed with other materials. Using a suitable filling machine, the mixture is filled into hard gelatin capsules (No. 3). Other doses may be prepared by increasing the filling weight and, if necessary, changing the size of the capsules accordingly.

| (c) Delayed-release tablets | mg/tablet |
|---|---|
| Active principle | 80 |
| Cutina HR* | 25 |
| Lactose B.P. | 142.5 |
| Magnesium stearate B.P. | 2.5 |
| Compression weight | 250.0 |

*Cutina HR is a type of microfine hydrogenated castor oil manufactured by Messrs. Sipon Products Ltd., London The medicament is sifted through a 250 μm sieve and mixed with the Cutina HR and the lactose. The mixed powder is moistened with technical methyl spirit 74 O.P. and granulated. The granulate is dried, sieved and mixed with the magnesium stearate. The oily granules are compressed by 8.5 mm diameter stamps to form tablets having a hardness of no more than 10 kp (Schleuniger Tester)

| (d) Injectable preparation for intravenous administration | |
|---|---|
| | % by weight/vol. |
| Active principle | 0.25 |
| Water for injection BP to | 100.00 |

Sodium chloride may be added to adjust the tonicity of the solution. The pH-value may be adjusted with dilute acid or alkali in such a way that maximum stability is obtained.

The solution is prepared, clarified and introduced under nitrogen into ampoules of suitable size which are fused. The injectable preparation is sterilized by heating in an autoclave using an acceptable cycle. Alternatively, the solution may be sterilized by filtration and filled into sterile ampoules under aseptic conditions.

| (e) Syrup | | mg/5 ml dose |
|---|---|---|
| Active principle | | 20.0 |
| Sucrose | | 2750.0 |
| Glycerol | | 500.0 |
| Buffer | | |
| Fragrance | as necessary | |
| Coloring matter | | |
| Preservative | | |
| Distilled water | | to 5.0 ml |

The active principle, the buffer, the fragrance, the preservative and the coloring matter are dissolved in some of the water. The rest of the water is heated to around 80° C. and the sucrose is dissolved therein. The mixture is cooled. The two solutions are mixed, adjusted to the required volume and clarified by filtration.

What is claimed is:

1. A heterocyclic compound corresponding to the following tautomeric formulae $$R^1R^2NAlk-Q-XY(CH_2)_m-\overset{NH}{\underset{}{C}}-NH-\overset{O}{\underset{\overset{\|}{O}}{S}}-R^3 \rightleftharpoons \quad (I)$$

$$R^1R^2NAlk-Q-XY(CH_2)_m-\overset{NH_2}{\underset{}{C}}=N-\overset{O}{\underset{\overset{\|}{O}}{S}}-R^3$$

in which
  $R^1$ represents linear $C_{1-6}$ aklyl or cycloalkyl and
  $R^2$ represents linear $C_{1-6}$ alkyl, or
  $R^1$ and $R^2$ together with the nitrogen atom to which they are attached represent piperidine or pyrrolidine
  Alk represents a straight-chain alkylene chain containing from 1 to 6 carbon atoms;
  Q represents a thiophene ring incorporated in the rest of the molecule by bonds in the 2- and 5- position, or in the 2- and 4-position,
  X represents methylene, Y represents sulfur and m=2 or 3;
  $R^3$ is an amino group or an arylamino group; or physiologically acceptable salts thereof.

2. A heterocyclic compound as claimed in claim 1, wherein $R^1$ represents $C_{1-3}$ alkyl or $C_{5-6}$ cycloalkyl and $R^2$ represents hydrogen, methyl or ethyl, or $R^1R^2N$ represents piperidine or pyrrolidine.

3. A heterocyclic compound as claimed in claim 1, wherein $R^3$ represents a p-aminophenyl group.

4. A heterocyclic compound as claimed in claim 2, wherein $R^3$ represents a p-aminophenyl group.

5. A heterocyclic compound as claimed in claim 1, wherein Alk represents methylene.

6. A heterocyclic compound as claimed in claim 4 wherein Alk represent, methylene.

7. A heterocyclic compound as claimed in claim 1, wherein Q represents a thiophene ring incorporated in the rest of the molecule by bonds in the 2- and 5-position, and the group XY $(CH_2)_m$ represents $CH_2$-S-$(CH_2)_{2-3}$.

8. A heterocyclic compound as claimed in claim 6, wherein Q represents a thiophene ring incorporated in the rest of the molecule by bonds in the 2- and 5-position, and the group XY$(CH_2)_m$ represents $CH_2$-S-$(CH_2)_{2-3}$.

9. A heterocyclic compound as claimed in claim 1 wherein Q represents a thiophene ring incorporated in the rest of the molecule by bonds in the 2- and 4-position, and the group XY$(CH_2)_m$ represents $CH_2$-S-$(CH2)_{2-3}$.

10. A heterocyclic compound as claimed in claim 6, wherein Q represents a thiophene ring incorporated in the rest of the molecule by bonds in the 2- and 4-position, and the group XY$(CH_2)_m$ represents $CH_2$-S-$(CH_2)_{2-3}$.

11. A compound in accordance with claim 1, wherein the compound is N-(p-aminobenzene-sulfonyl)-3-[(2-N,N-dimethylaminomethyl-thienyl-4)-methylthio]-propionamidine or a physiologically acceptable salt thereof.

12. A compound in accordance with claim 1, wherein the compound is N-sulfamoyl-3-[(2-N,N-dimethyl-aminomethylthienyl-4)-methylthio]-propionamidine or a physiologically acceptable salt thereof.

13. A compound in accordance with claim 1, wherein the compound is N-sulfamoyl-3-[(2-(1-piperidinylmethyl)-thienyl-4)-methylthio]-propionamidine or a physiologically acceptable salt thereof.

14. A compound in accordance with claim 1, wherein the compound is N-(p-aminobenzene-sulfonyl)-3-[(2-(1-piperidinylmethyl)-thienyl-4-)-methylthio]-propionamidine or a physiologically acceptable salt thereof.

15. A compound in accordance with claim 1, wherein the compound is N-sulfamoyl-[(2-piperidinylmethyl-thienyl-4)-methylthio]-propionamidine or a physiologically acceptable salt thereof.

16. A compound in accordance with claim 1, wherein the compound is N-(p-aminobenzene-sulfonyl)-3-[(2-piperidinylmethyl-thienyl-4-methylthio]-propionamidine or a physiologically acceptable salt thereof.

17. A process for producing the compounds claimed in claim 1, comprising reacting a compound corresponding to the following general formula

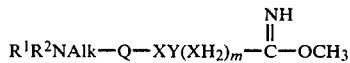 (II)

in which $R^1$, $R^2$, Alk, Q, X, Y and m are as defined in claim 1, with a sulfonamide corresponding to the following formula

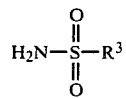 (III)

in which $R^3$ is as defined in claim 1.

18. The process of claim 17, which further comprises converting the compounds obtained upon reaction into a physiologically acceptable salt.

19. A mediacment inhibitor for histamine-$H_2$-receptors comprising an inhibitor for histamine-$H_2$-receptors effective amount of a compound of claim 1 and at least one inert, pharmaceutically acceptable support or inert, pharmaceutically acceptable diluent.

* * * * *